US010769559B2

(12) United States Patent
DeSimas et al.

(10) Patent No.: US 10,769,559 B2
(45) Date of Patent: Sep. 8, 2020

(54) SYSTEMS AND METHODS FOR GENERATING AUTOMATED SOFTWARE WORKFLOW FOR BIOLOGICAL TESTING (71) Applicant: APPLIED BIOSYSTEMS, LLC, Carlsbad, CA (US)

(72) Inventors: Bruce DeSimas, Danville, CA (US); Leslie Dow, La Honda, CA (US)

(73) Assignee: Applied Biosystems, LLC, Carlsbad, CA (US)

(*) Notice: Subject to any disclaimer, the term of this patent is extended or adjusted under 35 U.S.C. 154(b) by 613 days.

(21) Appl. No.: 14/859,001

(22) Filed: Sep. 18, 2015

(65) Prior Publication Data

US 2016/0086106 A1 Mar. 24, 2016

Related U.S. Application Data (63) Continuation of application No. 13/069,560, filed on Mar. 23, 2011, now abandoned, which is a continuation of application No. 11/593,695, filed on Nov. 7, 2006, now abandoned.

(60) Provisional application No. 60/734,089, filed on Nov. 7, 2005.

(51) Int. Cl.
*G06G 7/48* (2006.01)
*G06F 15/00* (2006.01)
*G06Q 10/06* (2012.01)
*C12Q 1/686* (2018.01)

(52) U.S. Cl.
CPC ............. *G06Q 10/06* (2013.01); *C12Q 1/686* (2013.01)

(58) Field of Classification Search
None
See application file for complete search history.

(56) References Cited

U.S. PATENT DOCUMENTS

| 5,061,639 | A | * | 10/1991 | Lung | G01N 35/00594 |
| | | | | | 177/245 |
| 5,333,675 | A | * | 8/1994 | Mullis | B01J 19/0046 |
| | | | | | 165/268 |
| 5,581,476 | A | * | 12/1996 | Osslund | C07K 1/00 |
| | | | | | 435/252.3 |
| 7,939,310 | B2 | | 5/2011 | Ginns et al. | |
| 2007/0112804 | A1 | | 5/2007 | DeSimas et al. | |
| 2011/0231758 | A1 | | 9/2011 | DeSimas et al. | |

OTHER PUBLICATIONS

Vossen, Gottfried, et al., The WASA Approach to Workflow Management for Scientific Applications, NATO Advanced Study Institute, Series F: Computer and System Sciences, 1997, pp. 1-22.
Steinlechner, Martin, et al., Automation and High Through-put for a DNA Database Laboratory: Development of a Laboratory Information Management System, Forensic Sciences, Croatian Medical Journal, 2001, pp. 252-255, vol. 42—iss. 2.

* cited by examiner

*Primary Examiner* — Anna Skibinsky
(74) *Attorney, Agent, or Firm* — Mauriel Kapouytian Woods LLP; Lana Akopyan; Michael Mauriel (57) ABSTRACT

The workflow application integrates with a research software application associated with a laboratory instrument to provide a user with step-by-step instructions on how to follow the workflow steps of a laboratory experiment. The instructions are dynamically tailored, according to the nature of the workflow, the samples being experimented upon and/or the operating states of the instrument and/or the research software application. The workflow application significantly reduces the learning curve to operate sophisticated laboratory instruments. In a genetic testing instrument the workflow application can prescribe the need for control samples and can optimize the layout of samples within the instrument's sample receiving plate or fixture.

8 Claims, 11 Drawing Sheets

| Presentation Layer | Setup Story | Pipette Story | Run Story | View Story | Template Story |
|---|---|---|---|---|---|
| Application Layer | Setup Manager | Pipette Manager | Run Manager | Results Manager | Template Manager |
| Services Layer | Sequence Detection System Server | | | Utilities | |

Create and Edit a Plate

Enter plate information -----☐

Select targets ---------☐

Enter sample names ------☐

Select pipetting option-----☐

Confirm plate configuration -☐

Select next step --------☐

Fig. 16

Pipette a Plate

Select a plate to pipette -------------------☐

Select a pipetting procedure---------------☐

Review reagent and sample information--------☐

Prpare premix solution-------------------☐

Pipette premix------------------------☐

Pipette unknown samples----------------☐

Pipette negative controls----------------☐

Close tubes before pipetting--------------☐
    positive controls
Pipette positive controls-----------------☐

Close tubes-------------------------☐

Confirm plate map---------------------☐

Select next step ---------------------☐

Fig. 17

Run a Plate
- Select a plate to run
- Run a plate
- Run in progress
- Run complete
- (If error) Run error

Fig. 18

View Results
- by well (plate view)
- by well (table view)
- by sample
- plate information
- report

Fig. 19

Create and Edit Template
- Select a template creation option
- Enter template information
- Select a template to edit
- Create template from plate
- Select targets
- Select pipetting option
- Select next step

SYSTEMS AND METHODS FOR GENERATING AUTOMATED SOFTWARE WORKFLOW FOR BIOLOGICAL TESTING

CROSS-REFERENCE TO RELATED APPLICATIONS

This application claims the benefit of U.S. Provisional Application No. 60/734,089, filed on Nov. 7, 2005. The disclosure of the above application is incorporated herein by reference.

INTRODUCTION

When performing biological testing some workflows may utilize sophisticated instruments that have heretofore proven difficult for unsophisticated users, such as bench technicians, to operate. By way of example polymerase chain reaction (PCR) testing is a molecular biology technique used in many biological testing applications. The technique employs sophisticated instruments that may require specialized knowledge in order to operate. The present teachings can be used to allow instrument operators to use these sophisticated devices without having specialized training or knowledge. The present teachings provide a simplified user interface that works in conjunction with more sophisticated software systems (such as those associated with PCR instruments). The simplified user interface hides highly technical information from the unsophisticated user, and yet permits a sophisticated user to readily access the underlying software system associated with the instrument, if desired.

These and other features of the present teachings are set forth herein. Further areas of applicability will become apparent from the description provided herein. It should be understood that the description and specific examples are intended for purposes of illustration only and are not intended to limit the scope of the present disclosure.

DRAWINGS

The skilled artisan will understand that the drawings, described below, are for illustration purposes only. The drawings are not intended to limit the scope of the present teachings in any way.

DESCRIPTION OF VARIOUS EMBODIMENTS

The following description is merely exemplary in nature and is not intended to limit the present disclosure, application, or uses. It should be understood that throughout the drawings, corresponding reference numerals indicate like or corresponding parts and features.

The present teachings can be used in a wide variety of different instruments, employed in a wide variety of different workflows. For purposes of illustration, and without intending to limit the teachings in any way, a PCR instrument will be used for the following description. Accordingly, in FIG. 1 PCR instrument 50 has been illustrated. Examples of such an instrument include the model 7300/7500 real-time PCR instruments available from Applied Biosystems, Inc. Of course, other types of instruments may also be used.

Figure 1:
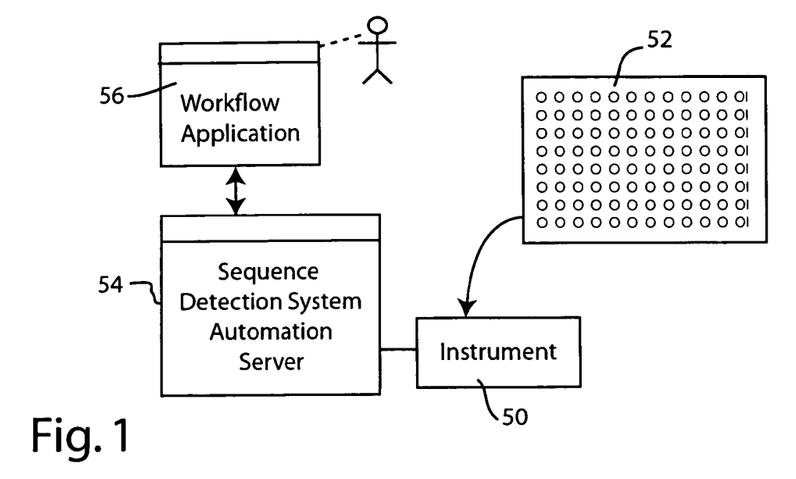
FIG. 1 is a block diagram illustrating the workflow application in conjunction with an exemplary biological testing instrument and supporting software system.

The PCR instrument 50 is designed to perform PCR analysis of samples that have been deposited in a multi-well plate 52. The instrument 50 works in conjunction with a research software application, such as sequence detection system (SDS) software that integrates with the instrument to control its operation and store, manipulate and analyze the resulting test data. The SDS software may be deployed on a suitable computer, either as a stand-alone computer dedicated to the instrument 50 or deployed on a suitable server. For illustration purposes, FIG. 1 depicts the SDS software residing on an automation server 54. A workflow application 56, configured according to the present teachings, communicates with the SDS software (e.g., automation server 54). As will be more fully explained, the workflow application is designed for an instrument operator whose education may range from a high school diploma to a Ph.D. The workflow application 56 is designed so that users need to have very little knowledge of biology, computers or of the specific instrument 50. The workflow application effectively hides much of the technical aspects of the SDS software, and instead provides a simple user interface that leads the user, step-by-step through the entire workflow process.

To begin to appreciate the power and convenience afforded by the workflow application 56, it is helpful to understand a little bit about the underlying SDS software with which the workflow application integrates. The SDS software for a PCR instrument, such as those identified above, is intimately concerned with all working aspects of the PCR instrument. A sophisticated operator of the SDS software would, for example, be able to analyze and reanalyze data, alter threshold values, change thermal cycling parameters (such as temperatures, times and number of cycles), view amplification plots, view standard curves (and all related data such as R2, slope and Y-intercept), read Ct values, read detectors, examine thermal cycling profiles, and the like. While these functions are important to the proper operation of the PCR instrument, they are topics that are well beyond the ken of the typical laboratory technician. While an SDS software system has been illustrated here, it will be appreciated that the teachings herein can be utilized with any research software application.

The workflow application 56, in effect, negotiates with and controls the SDS software system on behalf of an unsophisticated user. In addition, the workflow application 56 provides the user with step-by-step instructions on how to carry out each part of a potentially sophisticated workflow. This is diagrammatically illustrated in FIG. 2.

Figure 2:
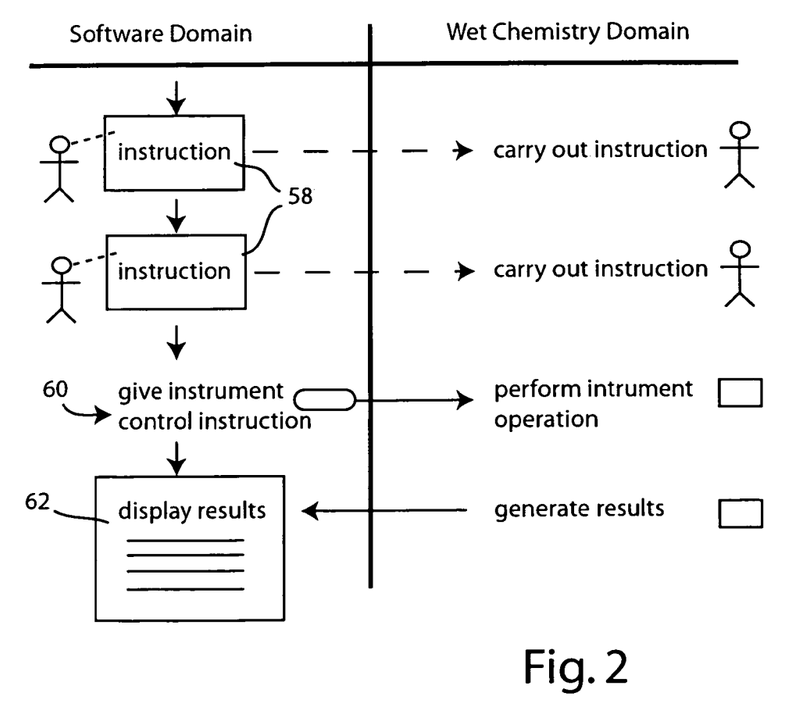
FIG. 2 is a domain diagram illustrating how the workflow application integrates the software domain with the wet chemistry domain.

Referring to FIG. 2, it can be seen that the workflow application defines a software domain and a wet chemistry domain. The workflow application functions within the software domain, while the laboratory technician performs workflow steps within the wet chemistry domain, based on guidance received from the workflow application in the software domain. Thus, as illustrated, the workflow application provides the technician with a series of instructions, in the form of on-screen displays based on tutorial story content. The user then carries out these instructions in the wet chemistry domain. Instructions are specifically configured for the particular workflow being performed. In this way, the technician is prompted at each step so that there is no confusion or ambiguity. The instructions given at 58 are more than simple static screens of information. Rather, the instructions are dynamically generated to automatically take into account workflow-specific options or other sample-specific or chemistry-specific aspects of the test being performed. For example, the instructions will automatically specify when negative or positive controls need to be utilized and the instructions even will optimize where the control and unknown samples should be located within the wells of the plate.

Once the technician has finished all of the steps needed to prepare and install the plate within the instrument, the workflow application can then automatically give the instrument control instruction to the SDS software, causing the SDS software to in turn, initiate the necessary instrument operations to effect the test. This is illustrated diagrammatically at 60. Finally, when the instrument results are obtained, those results are communicated to the workflow application, allowing the user to view the displayed results in a user-friendly, graphical format, as at 62.

The workflow application is designed to load data into the underlying research software application (such as the SDS software of a PCR instrument) and this way the workflow application has knowledge of the test conditions that are assigned to the research software application. By way of illustration, see FIG. 3. The workflow application 56 may be initially configured to contain information on how certain standard or frequently used tests are performed. For such tests, the workflow application stores the workflow steps and associated parameter settings that allow the workflow application to not only guide the user but also configure the underlying research software application (e.g., SDS). The workflow application is made considerably more flexible by the ability to import new tests and associated parameter settings. One convenient way to provide such additional test and parameter setting information is to supply the information as target information associated with a specific chemistry kit. The chemistry kit and corresponding target information can be supplied as part of a package or module, such as a package or module devoted to a particular pathogen, for example. This has been illustrated at 64 in FIG. 3. In the illustrated embodiment, the target information may be supplied on suitable computer-readable media, such as a CD-ROM 66. Alternately, the target information could be supplied via a portal accessible via a network such as the internet.

Figure 3:
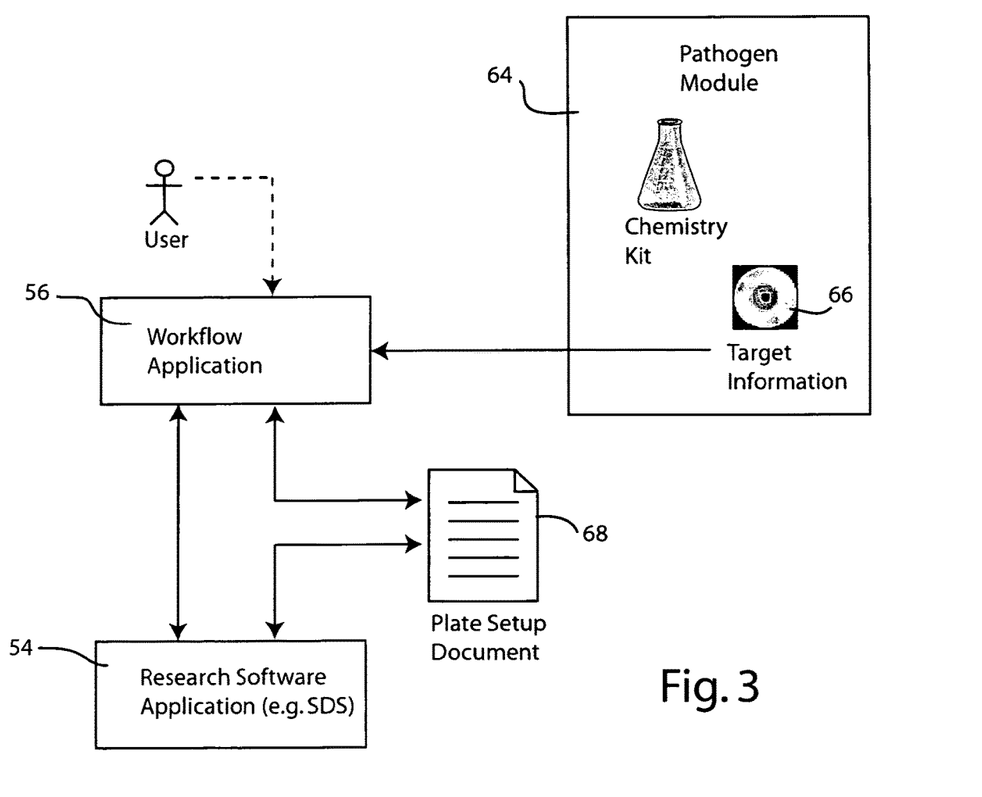
FIG. 3 is a block diagram further illustrating the workflow application and how target information may be supplied in connection with a pathogen module.

By way of example, the workflow application 56 might be configured to perform standard tests for a predefined set of organisms (e.g., *Listeria monocytogenes, Campylobacter jejuni, Salmonella, E. Coli* O157:H7). If the particular instrument needs to be outfitted with the capability to analyze a different pathogen, such as anthrax, a pathogen module 64 would be provided and the associated target information 66 would then be uploaded into the workflow application.

The workflow application establishes and saves a plate setup document 68 that contains data about the particular test to be performed. Some of the data is relevant to the research software application 54. Thus the research software application reads the plate setup document, utilizing the information that is relevant to it and ignoring what is not.

In addition to communicating through the shared plate setup document 68, the research software application (e.g., SDS) may also be configured to communicate directly with the workflow application. This may be effected in a variety of ways. One possible embodiment has been illustrated in FIG. 4.

Figure 4:
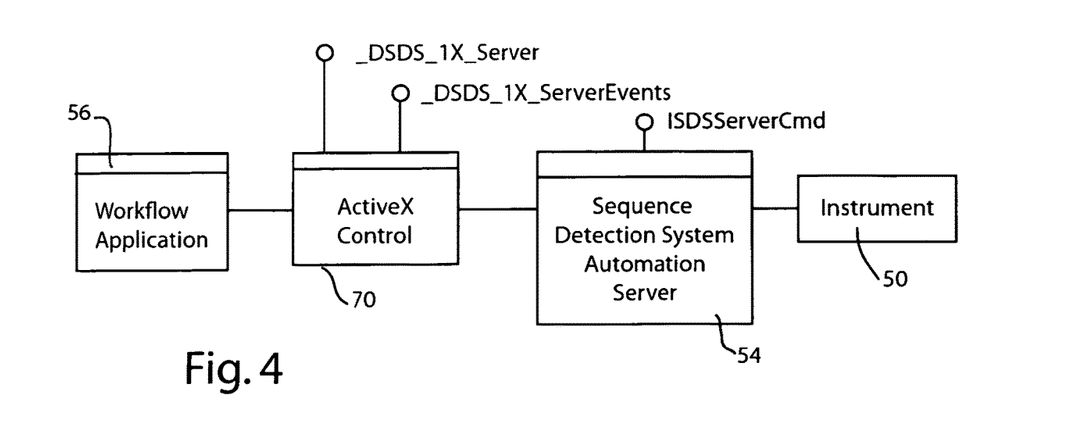
FIG. 4 is a block diagram illustrating an implementation using Component Object Model or ActiveX technology.

Referring to FIG. 4, the workflow application and the SDS software may communicate using a message passing protocol, such as may be implemented using Active X controls. Using Active X technology, depicted diagrammatically at 70, the SDS automation server 54 and workflow application 56 can communicate with each other. The Active X technology components utilize the Distributed Component Object Model (DCOM) standard defined by Microsoft Corporation. Alternatively, other types of messaging systems and object interaction systems may be utilized.

Those of skill in the art will recognize that different software architectures may be used to implement the workflow application. One such architecture has been illustrated in FIG. 5. As illustrated, the workflow application may be functionally broken down into layers, including a services layer, an application layer and a presentation layer. Specifically, at the outermost layer (presentation layer) the user interface presents a series of "stories" that a user follows. Each story is made up of a sequence of pages which in turn may be displayed in a wizard-style dialogue. These dialogues handle a given workflow instruction or workflow process, such as instructing the user on setting up a plate, pipetting a plate, running a plate in the instrument, viewing the results, and so forth.

Figure 5:
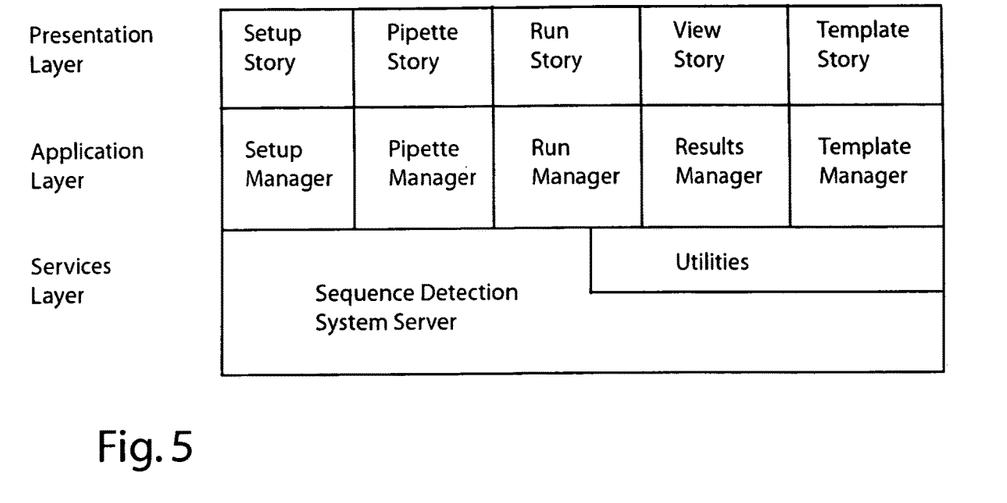
FIG. 5 is a software architectural diagram illustrating how the workflow application may be configured.

Stories rely on one or more "managers" to simplify and provide a coherent way to manipulate and manage the data making up the user interface content. These managers reside within the application layer. The managers are configured to provide the basic functionality of the workflow application. For example, the setup manager validates whether a duplicate sample name is trying to be entered on behalf of the user interface components. The setup manager also provides a user interface (presentation layer) with information on the kinds of targets that are available. This is based on what the setup manager ascertains by reading the plate setup document and other initiation files. Managers also handle the saving and retrieving of sample data, plate layouts and other items of user interface content.

The managers make calls to various utilities on behalf of the stories being presented. The managers formulate final names, initialize files and make calculations, as required, so that these details are encapsulated and thus hidden from the stories and pages. The managers handle all calls to the SDS server on behalf of the stories. For example, the run manager handles messaging back and forth between the server and the user interface when driving a plate through a thermo-cycling operation.

Figure 6:
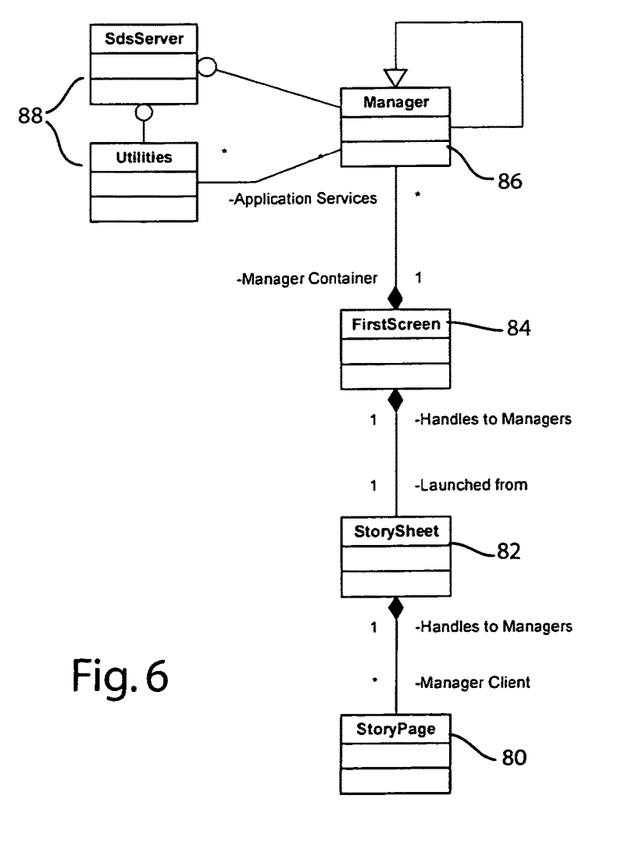
FIG. 6 is a class diagram useful in understanding the manager classes implemented in the architecture of FIG. 5.

If desired, the managers within the application layer can be developed based upon an object-oriented class. An exemplary manager class has been illustrated in FIG. 6. In the illustrated manager class diagram, the story page 80 uses (or reuses) any number of story pages (text, diagrams, video clips, sound files and the like) to form a wizard-style dialogue. A story sheet 82 relays requests to the first screen 84 for creating and getting handles to managers 86 made by pages. At some point in a wizard dialogue, typically at the beginning, makes a request through the story sheet 82 for a first screen 84 to create a manager. Both the first screen and the story sheet are singletons. At any moment the first screen may have created and thus contain zero or more managers. Managers may be subclasses of one another and accessed by any page in any story. The managers may access the SDS server and utilities 88 of the services layer (FIG. 5) for loading and saving files, generating file names, performing calculations, and so forth. A manager may also handle messaging to and from the SDS server on behalf of a page.

Figure 7:
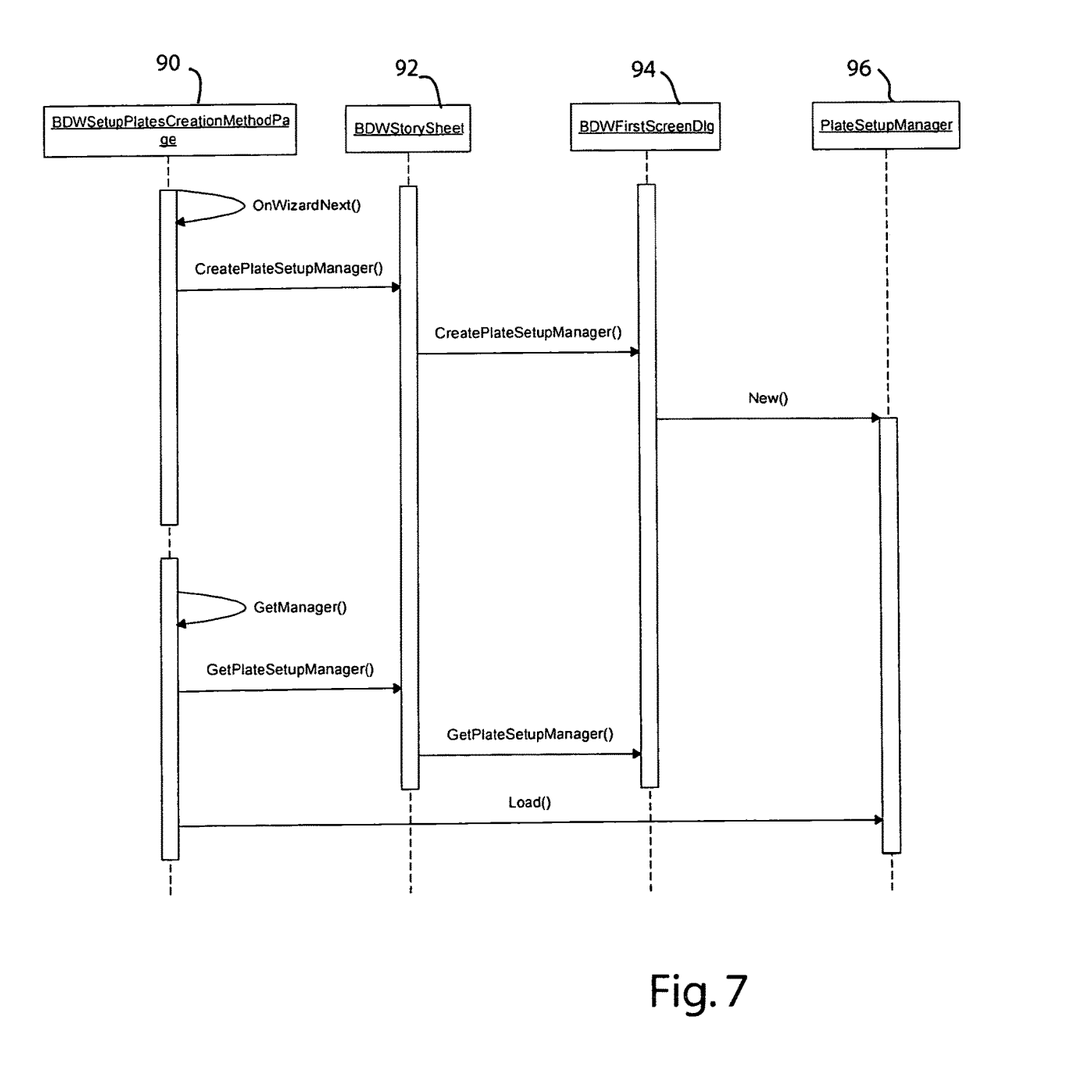
FIG. 7 is a sequence diagram illustrating an exemplary manager life cycle.

The managers have a life cycle that may be better understood with reference to FIG. 7. Specifically, FIG. 7 shows how the setup manager is created and accessed to perform a setup plate operation. The sequence diagram of FIG. 7 shows the methods that are invoked to create a setup plate manager and the subsequent calls by the page to the manager to execute a Load instruction of an existing plate for use with the Setup Story. As illustrated, the setup plate creation object 90, associated with a story page, sends a create plate message to the story sheet object 92, which in turn sends a create plate message to the first screen dialogue object 94, which in turn sends a New command to the plate setup manager object 96. Thereafter, the setup plate creation object 90 sends a get plate setup manager message to the story sheet object 92, which in turn sends a get plate setup manager message to the first screen dialogue object 94. Thereafter, the story page 90 sends a Load instruction to the plate setup manager 96.

Figure 8:
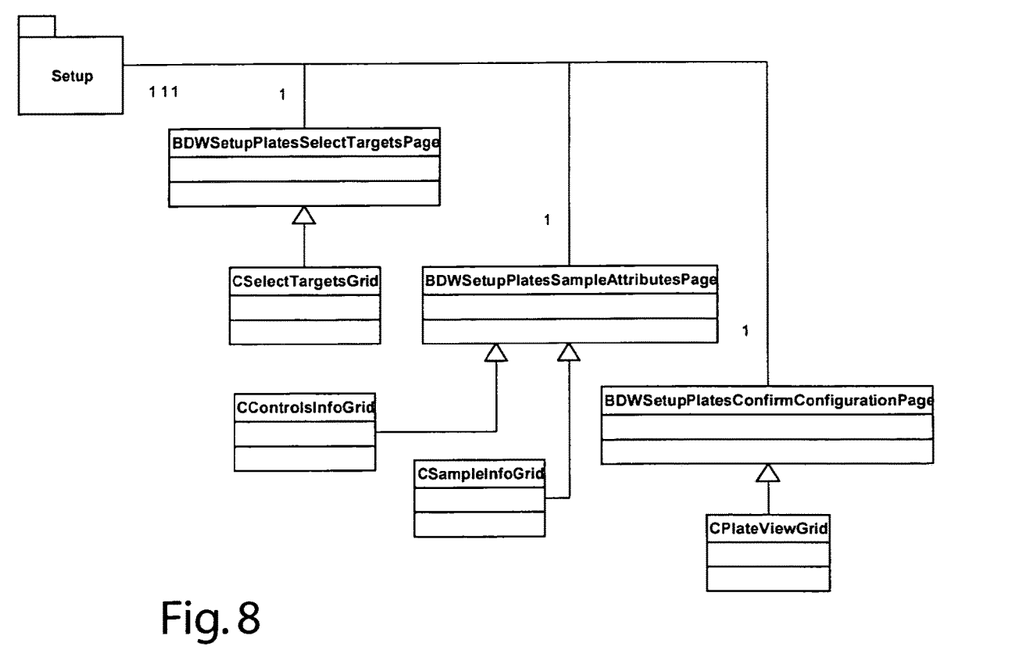
FIG. 8 is an object diagram illustrating a Setup object useful in implementing a workflow application.
Figure 9:
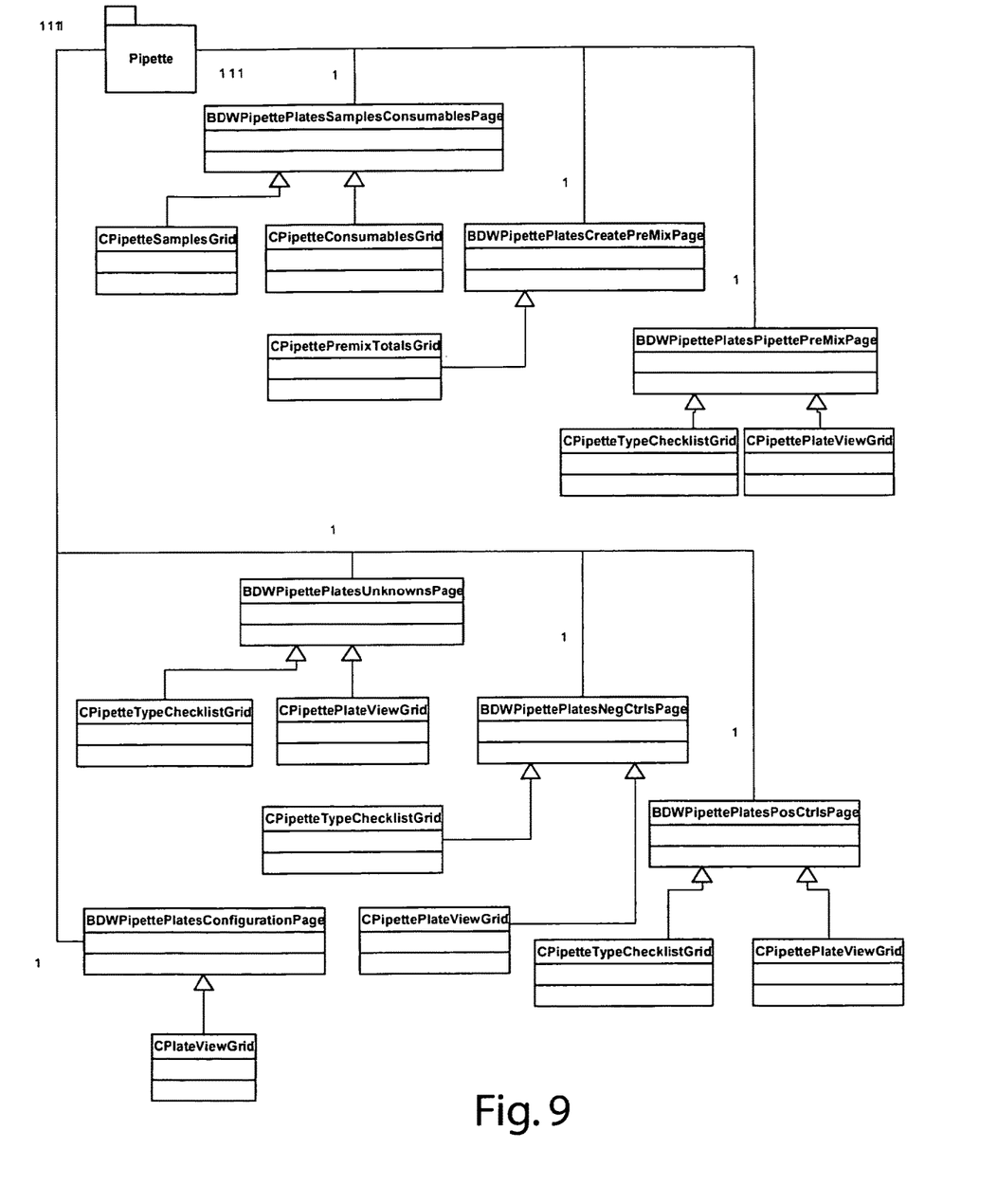
FIG. 9 is an object diagram illustrating a Pipette object useful in implementing a workflow application.
Figure 10:
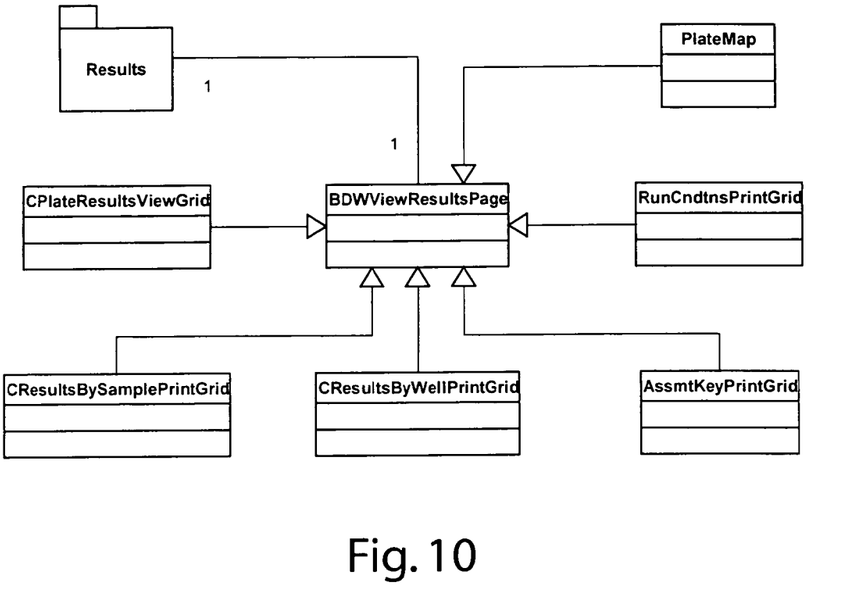
FIG. 10 is an object diagram illustrating a Results object useful in implementing a workflow application.
Figure 11:
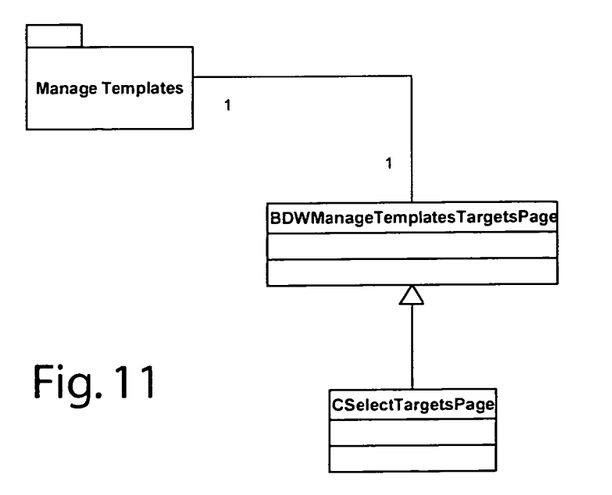
FIG. 11 is an object diagram illustrating a Manage Templates object useful in implementing a workflow application.

The setup object may be configured as shown in FIG. 8. The Pipette object may be configured as shown in FIG. 9. The results object and the manage template object may be configured as shown in FIGS. 10 and 11, respectively. It will be understood that the object-oriented configurations shown here are merely examples of how the various managers within the application layer (FIG. 5) may be implemented.

In one embodiment, user interface grids are used to convey information in an orderly fashion. While there are many ways to implement a grid interface structure, one useful technique involves use of a grid software component known as the Ultimate Grid, available from Hallogram Publishing, Inc. Grids are used to show/select target, sample, and controls information in the Plate Setup Process. In these grids they are used mostly to list collections of information. The grid is also used in a plate map view to represent the plate and the entities that will reside on that plate. The plate map view is a grid that looks like a plate, with each grid cell representing a well on the plate.

In the Pipette Process, grids are used to show reagent and sample information, premix solution information, premix volumes by well, unknown volumes by well, and control volumes by well. There are also many plate map views representing the plate and the premix volumes, sample volumes, and controls volumes on the plate by location. There is also a final pipette plate map view showing the plate and all of its contents.

In the Results View Process, a grid is used again as a plate view representation of the results of a plate. Each grid cell displays the results of the well it represents. Grids are also used for printing. Information that is normally displayed in grids in various fashions is organized in similar ways in grids that show the information in ways necessary to generate reports.

The grid may be implemented as a software class having the following structure:
    Base Grid Control
    Base Plate View Grid
        Plate View Grid
        Pipette Plate View Grid
        Plate Results View Grid
    Base Pipette Type Checklist Grid
        Pipette Premix Checklist Grid
        Pipette Type Checklist Grid
    Select Targets Grid
    Controls Info Grid
    Sample Info Grid
    Pipette Consumables Grid
    Pipette Samples Grid
    Pipette Premix Totals Grid
    Results by sample Print Grid
    Results by well Print Grid
    Utility Print Grid Each of the managers within the application layer (FIG. 5) is designed to interface with its respective "story" within the presentation layer. Each manager can also interface the underlying SDS software and associated utilities, if needed, to supply the appropriate information and guidance to the user. The managers do more than merely provide the user with a story to guide them in performing the prescribed steps of the workflow. The managers also perform computations, unique to the tasks being performed, to inject expert knowledge into the workflow.

For example, the pipette manager is able to instruct the user on where to put the different unknown samples and control samples, so that use of the plate is optimized. In one embodiment, optimization of plate usage is handled by following a predetermined set of rules governing how samples and controls should be distributed.

Exemplary rules for distributing samples and controls in a plate may include:
    If enough space is available, separate different targets by a row.
    If possible put at least one well between the unknowns and the controls.
    Separate negative controls from positive controls by one well, if possible.
    Place replicates of one sample for the same target next to each other.
    Start with the unknowns and put controls at the end.
    If possible, put positive controls at one of the outer rows or columns.
    Consider as well that users will use either strips of 8 or strips of 12 caps to close the tubes if they don't use a complete plate.

Note that, in some instances, it may not be possible to adhere to all of the sample distribution rules. In such case, the pipette manager determines the optimum set of rules that can be adhered to under the circumstances. Rules can have predetermined weights which can be used in determining which rules take precedence over others, when all rules are incapable of being followed in a particular case.

It will be recognized that the use of rules to optimize plate layout allows experiments to be performed in an optimal way, which would probably not be readily apparent to most system users.

The pipette manager also includes computational components that calculate the volumes of reagents needed to pipette the number of samples and controls specified for the selected plate. The user can specify a percent overage value to include an additional 1-10% in the environmental master mix (EMM) and target assay mix (TAM) volumes, if desired, to compensate for pipetting error when creating the premix solutions.

The setup manager also embeds expert system functionality to inject expert knowledge into the workflow. As previously mentioned, the SDS software is a highly sophisticated program that would not be readily understood by most users. The setup manager neutralizes this unfamiliarity by providing the user with a series of more easily answered questions. The setup manager takes the answers to those questions and determines how to properly configure the SDS software on behalf of the user. For example, the setup manager will automatically determine and specify the minimum number of controls (e.g., negative controls) that are required for the assay.

The results manager similarly embeds expert system functionality. The results manager can interpret the complex output from the SDS software and distill that output into simple graphical views showing basic information that a non-technical user would want to know, such as whether a particular pathogen is present in the unknown sample or not.

The run manager likewise embeds expert system functionality, but taking control of the instrument. Instead of needing to know how to run an experiment using the SDS software—which might entail many different steps that must be followed in the correct sequence—the run manager gives the user a simple "Start" button. When this button is pressed, the run manager takes charge and performs the proper run steps in the proper sequence for the user.

Figure 12:
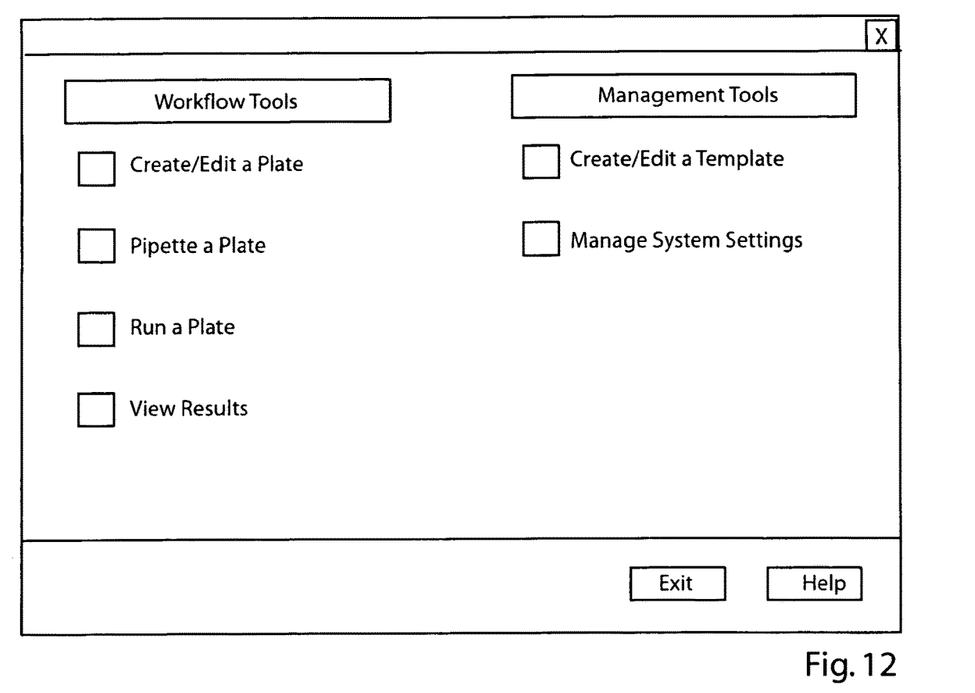
FIG. 12 is an exemplary user interface screen, showing how a workflow application may provide the user with initial choices.

Referring now to FIGS. 12-19, exemplary user interface screens will now be discussed, together with exemplary workflows according to the basic functions provided by the managers illustrated in FIG. 5. Referring first to FIG. 12, an exemplary first screen is illustrated. For convenience the screen has been subdivided into a section involving Workflow Tools and a section involving Management Tools. Of course, other organizations and layouts are also possible.

Figure 17:
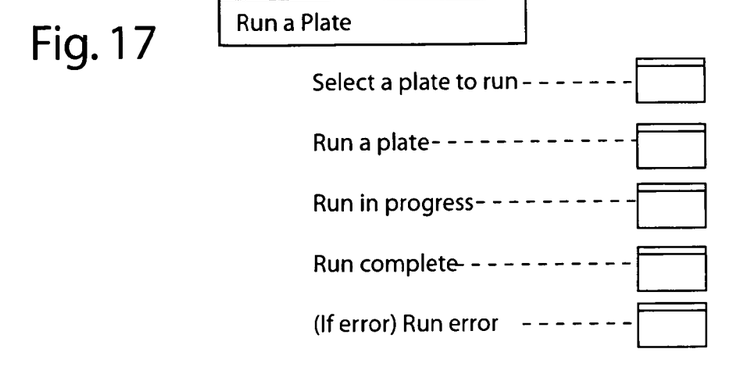
FIG. 17 is an exemplary flow diagram, showing steps that may be implemented by a Run a Plate workflow.
Figure 18:
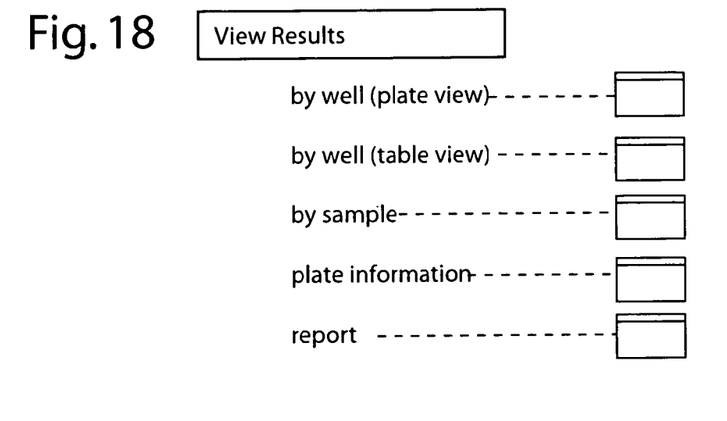
FIG. 18 is an exemplary flow diagram, showing steps that may be implemented by a View Results workflow.
Figure 19:
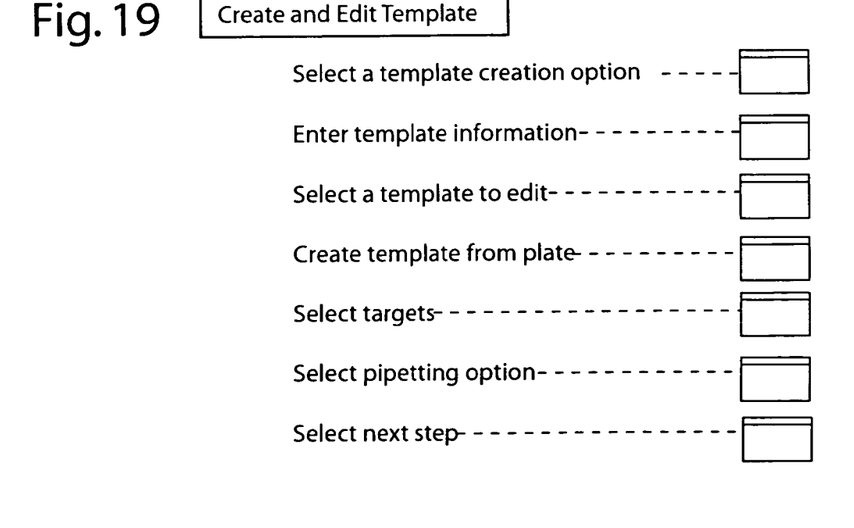
FIG. 19 is an exemplary flow diagram, showing steps that may be implemented by a Create and Edit Template workflow.

When the user selects one of the functions listed, the associated manager (FIG. 5) is invoked. For example, if the Create/Edit a Plate function is selected, the user will be presented with a series of screens of information that follow a basic workflow sequence illustrated in FIG. 15. Similarly, if the user selects Pipette a Plate, the user will be presented with a series of screens according to the workflow of FIG. 16. FIGS. 17-19 give examples of some of the additional workflows that may be selected from the first screen of FIG. 12. Each step in the workflow would have at least one display screen associated with it. Within that display screen, dialog boxes may pop up, as needed to induce user interaction if needed.

Figure 13:
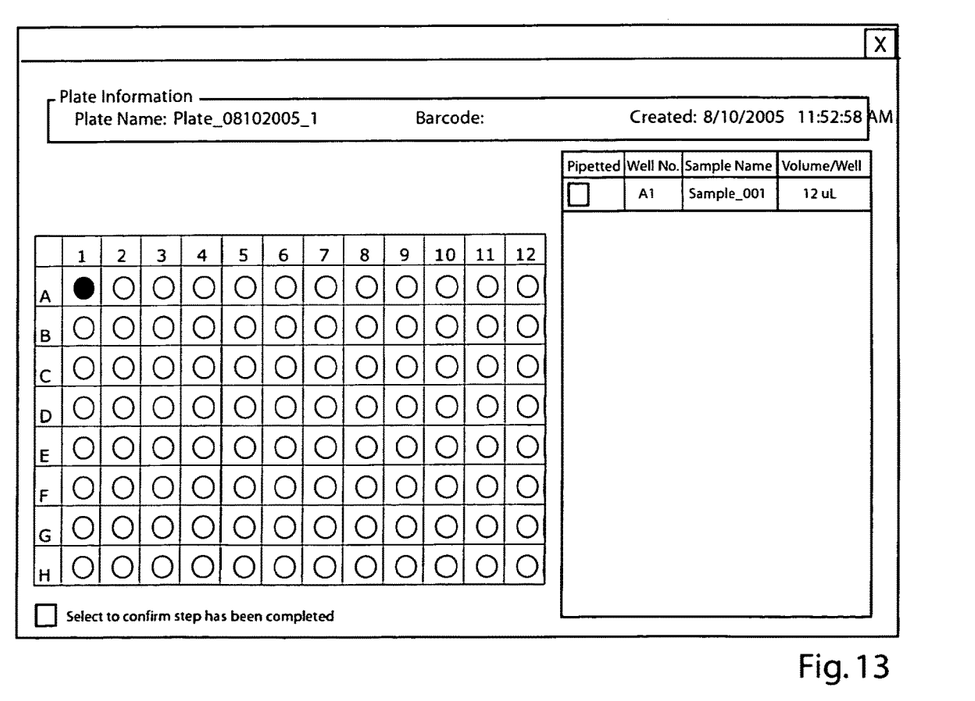
FIG. 13 is an exemplary user interface screen featuring visual depiction of plate wells.
Figure 14:
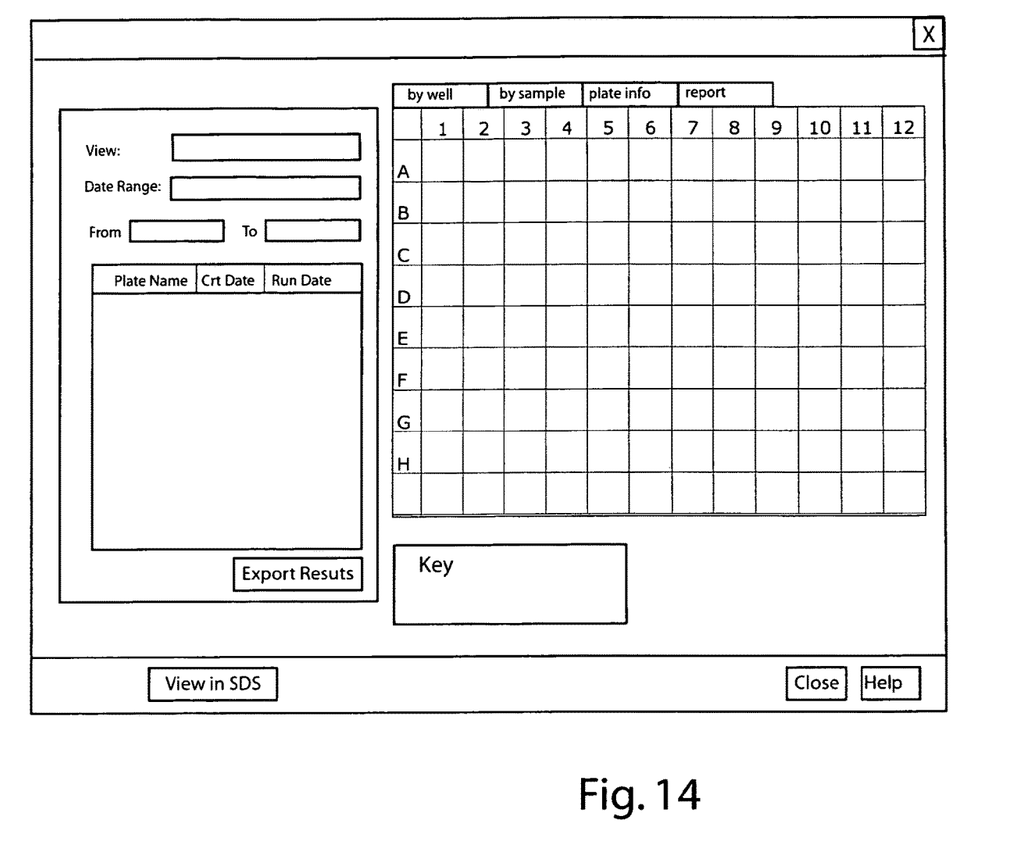
FIG. 14 is an exemplary user interface screen featuring various options for viewing results of sample analysis.
Figure 15:
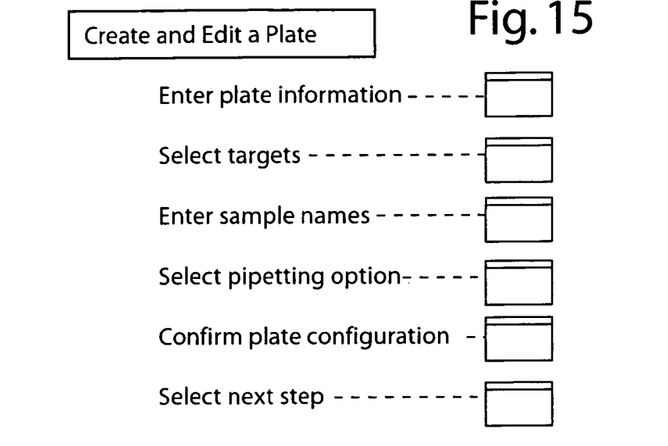
FIG. 15 is an exemplary flow diagram, showing steps that may be implemented by a Create and Edit Plate workflow.
Figure 16:
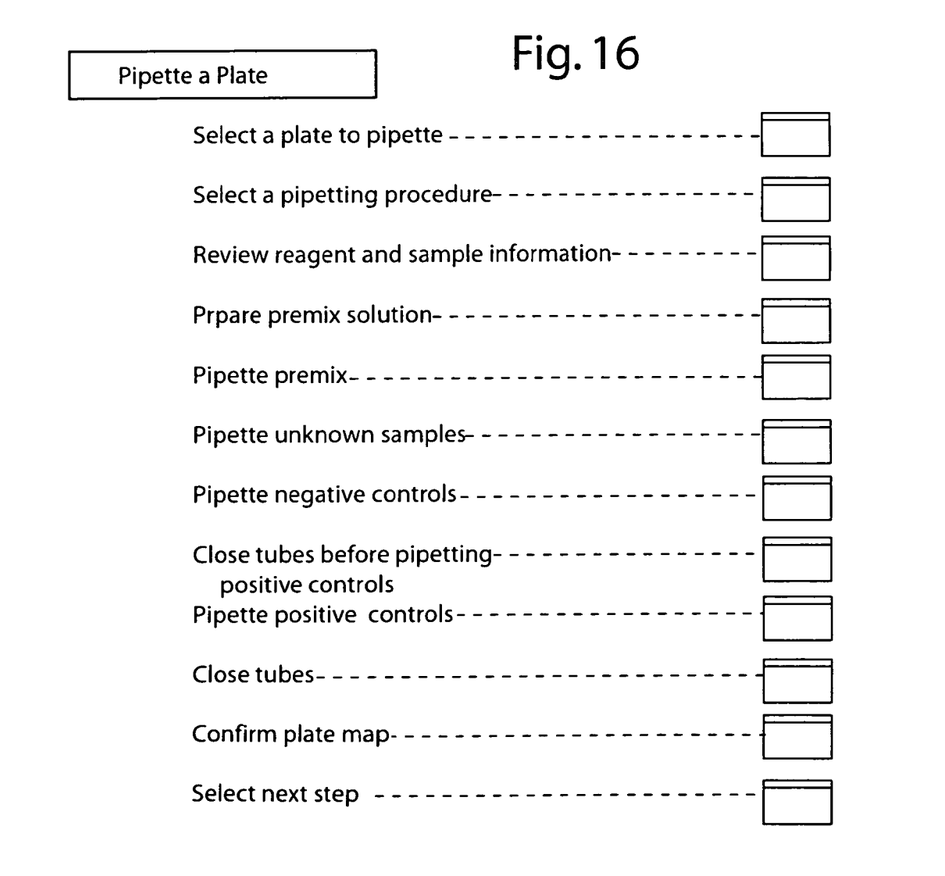
FIG. 16 is an exemplary flow diagram, showing steps that may be implemented by a Pipette a Plate workflow.

To maintain a consistent look and feel, the individual screens corresponding to the individual steps in each of the workflows (of FIGS. 15-19) may be based on a set of common layouts. For illustration purposes, two exemplary layouts have been provided in FIGS. 13 and 14. FIG. 13 features a graphical grid resembling the wells of the instrument plate (FIG. 1). FIG. 14 features a graphical grid, similar to a spreadsheet layout, for displaying the results of an experiment. Tabs at the top of the spreadsheet grid may be selected to show results grouped in different ways. Illustrated here are tabs to display results by well, or by sample.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed is:

1. A computer program product comprising instructions encoded on a non-transitory machine readable medium, the instructions being executable on one or more processors to implement processing comprising:
    setup manager processing to ascertain the nature of an experimental workflow including storing associated parameter settings and target information, and automatically generating plate setup information; wherein:
        the associated parameter settings include thermocycling parameters for a particular experiment to be performed using a PCR instrument,
        the target information is associated with a specific chemistry kit for a particular target molecule associated with the particular experiment,
        automatically generating the plate setup information includes calculating an optimal volume for each component and determining an optimal layout of wet chemistry components within a test fixture of the PCR instrument based on a set of rules that specify, for the particular PCR experiment: a number and distribution of samples and positive and negative controls in a plate configuration;
    pipette manager processing to provide user instructions on how to physically deploy wet chemistry components within the test fixture of the PCR instrument; and
    run manager processing to control the PCR instrument in performing an experimental workflow, including automatically sending a control instruction and associated parameter settings including the plate setup information to the PCR instrument to perform the particular experiment, based on the determined associated parameter settings, upon the wet chemistry components within the test fixture wherein the test fixture is installed within the PCR instrument.

2. The computer program product of claim 1 further comprising interface adapted to couple to a research software application associated with a research instrument.

3. The computer program product of claim 2 wherein said run manager controls said laboratory instrument by communicating information to said research software application via said interface.

4. The computer program product of claim 2 further comprising a results manager adapted to process results obtained from a laboratory instrument used to perform an experimental workflow upon wet chemistry components within a test fixture wherein said results manager receives said results obtained from a laboratory instrument via said interface.

5. The computer program product of claim 1 wherein said pipette manager is adapted to optimize the physical layout of a laboratory experiment by providing tailored instructions to the user regarding said physical layout of the wet chemistry components within the test fixture.

6. The computer program product of claim 1 wherein the PCR instrument employs a multi-well plate to receive samples and wherein said pipette manager optimizes the placement of samples within said plate by providing tailored instructions to the user on where to place the samples.

7. The computer program product of claim 1 wherein said setup manager automatically determines the requirements for control samples to be included in a laboratory experiment and provides tailored instructions to the user regarding inclusion of such control samples within said experiment.

8. The computer program product of claim 1 wherein the set of rules specify, based on total available wells, well spacing between samples being tested for different target molecules and between samples and controls.

\* \* \* \* \*